United States Patent [19]

Bühler et al.

[11] 4,260,545

[45] Apr. 7, 1981

[54] N-SUBSTITUTED HALOGENOMETHYLENEINDOXYLS

[75] Inventors: Niklaus Bühler, Rheinfelden; Hans Bosshard, Basel; Alfred Sallmann, Bottmingen, all of Switzerland

[73] Assignee: Ciba-Geigy Corporation, Ardsley, N.Y.

[21] Appl. No.: 876,376

[22] Filed: Feb. 9, 1978

[30] Foreign Application Priority Data

Feb. 11, 1977 [LU] Luxembourg .......................... 76755

[51] Int. Cl.³ .......................................... C07B 209/18
[52] U.S. Cl. .................. 260/326.13 C; 260/326.13 F
[58] Field of Search ................................ 260/326.13 C Primary Examiner—Donald G. Daus
Assistant Examiner—D. B. Springer
Attorney, Agent, or Firm—Luther A. R. Hall

[57] ABSTRACT

Novel N-substituted halogenomethyleneindoxyls [N-substituted halogeno-(3-oxa[2H]indol-2-ylidene)-acetic acids] and a novel process for their preparation by reacting N-substituted anilides with dihalogenomaleic anhydrides or derivatives thereof are described. The novel N-substituted halogenomethyleneindoxyls are valuable intermediates for the preparation of pharmaceutical active compounds having an antiallergic action.

14 Claims, No Drawings

N-SUBSTITUTED HALOGENOMETHYLENEINDOXYLS

The present invention relates to novel N-substituted halogenomethyleneindoxyls [N-substituted halogeno-(3-oxa-[2H]-indol-2-ylidene)-acetic acids] and a novel process for their preparation.

The novel N-substituted halogenomethyleneindoxyls are of the formula I

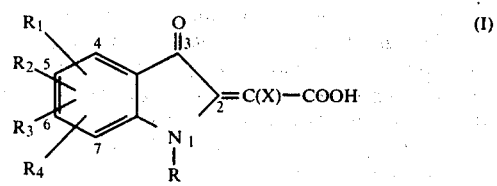

in which X is chlorine, bromine or fluorine and R is a substituted or unsubstituted lower alkyl group or a 5-membered to 7-membered cycloalkyl group and in which either $R_1$ is a lower alkyl group, a halogen atom or a hydroxyl, lower alkoxy, phenoxy or cycloalkyl group, $R_2$ is hydrogen or a lower alkyl, lower alkoxy or hydroxyl group and $R_3$ and $R_4$ independently of one another are hydrogen or a lower alkyl group and at least one of $R_1$ to $R_4$ is a lower alkyl group bonded to the benzene ring in the 5-position or 6-position, or $R_1$ and $R_2$ together are alkylene having 3–5 carbon atoms which is bonded to two adjacent carbon atoms and $R_3$ and $R_4$ are hydrogen.

The compounds according to the invention can be in the form of the cis or the trans isomers or in the form of mixtures of cis/trans isomers relative to the exocyclic C═C double bond. Mixtures of isomers of this type can be separated into their constituents on the basis of the differences in the physicochemical properties, in a conventional manner, for example by chromatography or by fractional crystallisation.

The compounds of the formula I can be prepared in high purity in a simple and economic manner using readily accessible starting materials and under mild reaction conditions, by reacting a compound of the formula II

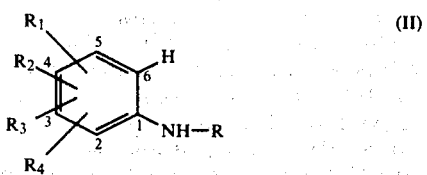

in the presence of a Lewis acid with a compound of the formula III

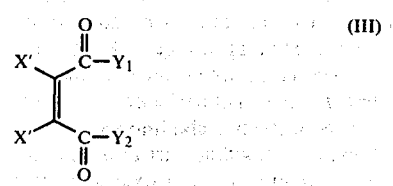

to give a compound of the formula IV

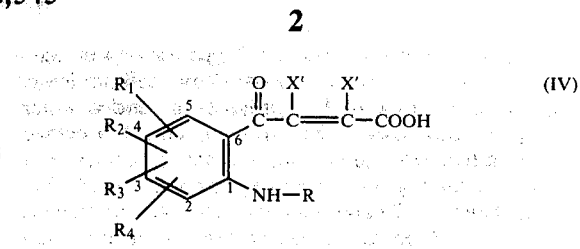

and subsequently cyclising the compound of the formula IV to a compound of the formula I.

In the above formulae II–IV, R, $R_1$, $R_2$, $R_3$ and $R_4$ are as defined under formula I, the two X' independently of one another are chlorine, bromine or fluorine and one of $Y_1$ and $Y_2$ is halogen, especially bromine or chlorine, and the other is —OH or —O-alkyl having 1–6 C atoms, or $Y_1$ and $Y_2$ together form the grouping —O—.

If $R_1$ is a lower alkyl group, a halogen atom or a hydroxyl, lower alkoxy, phenoxy or cycloalkyl group, $R_2$ is hydrogen or a lower alkyl, lower alkoxy or hydroxyl group and $R_3$ and $R_4$ independently of one another are hydrogen or a lower alkyl group, at least one of the radicals $R_1$ to $R_4$ in formula II and IV is a lower alkyl group bonded to the benzene ring in the 3-position or 4-position.

X and X' are preferably bromine and especially chlorine. $Y_1$ and $Y_2$ together preferably form the grouping —O—.

Lower alkyl groups as $R_1$ to $R_4$ and lower alkoxy groups as $R_1$ or $R_2$ have in particular 1–7 and preferably 1–4 carbon atoms, such as the methyl, ethyl, n-propyl, isopropyl, n-butyl, n-pentyl, n-heptyl, methoxy, ethoxy, n-propoxy, isopropoxy, n-butoxy, tert.-butoxy, n-pentyloxy and n-hexyloxy group. Particularly preferred lower alkyl and lower alkoxy groups have 1 to 2 carbon atoms, in particular the methyl group and the methoxy group.

If $R_1$ is a halogen atom, this is in particular halogen having an atomic number of up to and including 35, i.e. fluorine, bromine and especially chlorine.

Preferred cycloalkyl groups $R_1$ are unsubstituted cycloalkyl groups having 5 to 8 ring carbon atoms, such as the cyclopentyl, cycloheptyl and cyclooctyl group and in particular the cyclohexyl group.

Phenoxy groups $R_1$ are preferably unsubstituted but can also be substituted by lower alkyl or lower alkoxy groups having 1–4 and especially 1 or 2 carbon atoms, such as the methyl or methoxy group, or by halogen atoms, for example chlorine.

Alkylene having 3 to 5 carbon atoms which is formed by $R_1$ and $R_2$ together is especially 1,3-propylene or 1,4-butylene or, less preferentially, 1,5-pentylene.

Possible substituents of lower alkyl groups R are, in particular, hydroxyl groups and lower alkoxy groups having 1–7 carbon atoms and one or more substituents can be present.

Hydroxy- or lower alkoxy-lower alkyl groups R are, in particular, 2- and/or 3-hydroxy-lower alkyl groups, for example 2-hydroxyethyl, 3-hydroxypropyl or 2,3-dihydroxypropyl, or 2-or 3-lower alkoxy-lower alkyl groups, such as 2-methoxyethyl, 2-ethoxyethyl or 3-methoxypropyl.

Cycloalkyl groups R are preferably unsubstituted but can also be substituted, for example by a methyl group or chlorine. R is particularly preferentially the cyclopentyl or cyclohexyl group.

Preferred compounds of the formula I are those in which X is a chlorine atom and R is lower alkyl having 1-4 carbon atoms, 2- and/or 3-hydroxy-lower alkyl having 2-4 carbon atoms or 2- or 3-lower alkoxy-lower alkyl having a total of 3-7 carbon atoms and in which either $R_1$ is a lower alkyl group having 1-4 carbon atoms, a halogen atom having an atomic number of up to and including 35, a hydroxyl group, a cycloalkyl group having 5-7 carbon atoms, especially cyclohexyl, or a lower alkoxy group having 1-4 carbon atoms and $R_2$, $R_3$ and $R_4$ independently of one another are hydrogen or a lower alkyl group having 1-4 carbon atoms and at least one of the radicals $R_1$ to $R_4$ is a lower alkyl group having 1-4 carbon atoms which is bonded in the 5-position or 6-position, or in which $R_1$ and $R_2$ together are alkylene having 3 to 5 carbon atoms which is bonded in the 5,6-position and $R_3$ and $R_4$ are hydrogen.

Particularly preferred compounds are those of the formula Ia

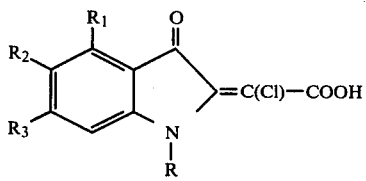

in which R is lower alkyl having 1-4 carbon atoms, 2- and/or 3-hydroxy-lower alkyl having 2-4 carbon atoms or 2- or 3-lower alkoxy-lower alkyl having a total of 3 or 4 carbon atoms and in which either one of the radicals $R_2$ and $R_3$ is lower alkyl having 1-4 carbon atoms, one of the remaining radicals $R_1$, $R_2$ and $R_3$ is hydrogen, lower alkyl having 1-4 carbon atoms, halogen having an atomic number of up to and including 35, lower alkoxy having 1-4 carbon atoms or hydroxyl and the last of the radicals $R_1$, $R_2$ and $R_3$ is hydrogen or lower alkyl having 1-4 carbon atoms, or in which $R_1$ is hydrogen and $R_2$ and $R_3$ together are alkylene having 3 or 4 carbon atoms.

Very particularly preferred compounds are those of the formula Ia in which $R_1$ is hydrogen or methyl and one of the radicals $R_2$ and $R_3$ is methyl and the other is hydrogen or methyl and R is as defined under formula Ia.

The starting materials of the formula II and III are known per se or can be prepared by conventional methods.

Compounds of the formula III which are preferably used are those in which the two X' have the same meaning and $Y_1$ and $Y_2$ together are the grouping —O—, and especially dichloromaleic anhydride.

Examples of Lewis acids which can be used when reacting the compounds of the formula II with the compounds of the formula III are: aluminium chloride, aluminium bromide, zinc chloride, tin tetrachloride, titanium tetrachloride, boron trifluoride, iron-III chloride, phosphorus trichloride, phosphorus oxychloride, antimony pentafluoride and antimony pentachloride. Aluminium chloride is preferably used.

The Lewis acid is appropriately employed in excess, for example in about 2 times to 10 times the molar amount. The reactants of the formula II and III are preferably employed in substantially stoichiometric amounts.

The reaction to give the intermediates of the formula IV can be carried out in an inert organic solvent or in the melt. Suitable organic solvents are, for example: chlorinated aliphatic or aromatic hydrocarbons, such as methylene chloride, 1,2-dichloroethane, 1,2,3-trichloropropane, 1,1,2,2-tetrachloroethane and o-dichlorobenzene; n-pentane and n-hexane; nitrobenzene, nitromethane and carbon disulphide.

The reaction in the melt is appropriately carried out in the presence of low-melting salt mixtures, for example mixtures of aluminium chloride with inorganic or organic salts, such as ammonium halides, alkaline earth metal halides and alkali metal halides, for example ammonium chloride, magnesium chloride and calcium chloride, but especially sodium chloride and potassium chloride, and also pyridinium salts, for example N-alkylpyridinium halides. Eutectic salt mixtures, especially mixtures of aluminium chloride and sodium chloride and/or potassium chloride, are preferred. However, in themselves any desired salt mixtures can be employed if an adequate lowering of the melting point is achieved therewith.

However, the reaction is preferably carried out in an inert organic solvent, especially methylene chloride, 1,2-dichloroethane or 1,1,2,2-tetrachloroethane.

In general, the reaction temperatures are between about 0° and 130° C. For the reaction in an inert organic solvent, reaction temperatures of between about 0° and 90° C. are preferred, depending on the nature of the solvent. In most cases, however, the reaction in the presence of an inert organic solvent can already be carried out at temperatures of between about 0° and 60° C.

The reaction in the melt is appropriately carried out at temperatures of between about 70° and 120° C. After the reaction has ended, the resulting complex is appropriately decomposed by pouring it into a water/ice mixture or by adding a dilute mineral acid, such as hydrochloric acid, with cooling, and the solvent, if present, is removed.

The cyclisation of the compounds of the formula IV with elimination of HX can be carried out in an organic or aqueous-organic medium. However, the cyclisation is preferably carried out in an aqueous medium.

The cyclisation temperature and time can vary greatly depending on the nature of the intermediate of the formula IV and of the reaction medium chosen.

Mixtures of a base, such as pyridine or triethylamine, with suitable inert organic solvents and, if desired, water are appropriately used for the cyclisation in an organic or aqueous-organic medium. Suitable inert organic solvents are, for example, aliphatic or aromatic hydrocarbons, which can be chlorinated, such as 1,2-dichloroethane, benzene, toluene and chlorobenzene; aliphatic or cyclic ethers, such as diethyl ether, tetrahydrofurane and dioxane; ethylene glycol monoalkyl and dialkyl ethers having, in each case, 1-4 carbon atoms in the alkyl parts, such as ethylene glycol monomethyl ether and ethylene glycol monoethyl ether, ethylene glycol dimethyl ether and ethylene glycol diethyl ether; or cellosolve.

In some cases it is appropriate to carry out the cyclisation in an aqueous medium in the presence of an organic or inorganic base. Examples of such bases which can be used are tertiary amines, such as triethylamine, pyridine, pyridine bases or alkali metal hydroxides or carbonates and alkaline earth metal hydroxides or carbonates. Alkaline earth metal hydroxides or carbonates and alkali metal hydroxides or carbonates are preferred, especially sodium hydroxide and potassium hydroxide and the corresponding carbonates.

In general, however, the addition of the said bases is superfluous. According to a particularly preferred embodiment, the cyclisation is carried out in an aqueous medium at a temperature of between about 0° and 100° C. and especially of between about 0° and 60° C.

After the reaction has ended, the compounds of the formula I can be isolated in a conventional manner, for example by acidifying the reaction mixture with hydrochloric acid or any other mineral acid, filtering and washing with water. The compounds of the formula I obtained by the process according to the invention in general contain only slight impurities and can be used direct for preparative purposes. If desired, they can be converted to the analytically pure form by recrystallisation from suitable solvents, such as anhydrous acetic acid, ethyl acetate, methanol, ethanol, dioxane or toluene.

The compounds of the formula I are obtained in the form of red to blackish crystals and are valuable intermediates for the preparation of pharmaceutical active compounds having an antiallergic action, for example N-substituted 3-hydroxyindolyl-2-glyoxylic acids and esters or salts thereof.

The preparation of several pharmaceutical active compounds which have antiallergic properties and can be used, for example, for the treatment and prophylaxis of allergic diseases, such as asthma, hay fever, conjunctivitis, urticaria and eczema, is described in the examples.

EXAMPLE 1

60 ml of 1,2-dichloroethane and 40 g (0.3 mol) of powdered anhydrous AlCl$_3$ are initially introduced into a stirred flask provided with a HCl outlet and cooled to 0° C. with an external ice/methanol bath. 13.5 g (0.1 mol) of N-methyl-3,4-dimethylaniline (freshly distilled) are then added dropwise at 0°–3° C. in the course of 20 minutes and the resulting suspension is stirred for 30 minutes at this temperature. 16.7 g (0.1 mol) of dichloromaleic anhydride (95% pure) are now added in small portions and the reaction mixture is stirred at 20°–25° C. for 20 hours. The resulting dark green solution is then poured onto about 500 g of ice, the mixture is stirred for 30 minutes and the aqueous phase is decanted off. 10 ml of ethyl acetate are added to the oily residue, whereupon violet crystals form. After filtering off and drying, 5.9 g of violet crystals having a melting point >220° C. are obtained. The resulting crystals are very pure and can be used direct for further reactions. Recrystallisation from suitable solvents, such as glacial acetic acid, is possible but not necessary.

NMR spectrum (100 Megahertz, δ values in ppm, DMSOd$_6$): 2.15 (s, 3H, CH$_3$); 2.30 (s, 3H, CH$_3$); 3.45 (s, 3H, NCH$_3$); 7.05 (s, 1H, aromatic); 7.30 (s, 1H, aromatic) COOH cannot be discerned in DMSOd$_6$).

The spectroscopic data from NMR, MS, IR and UV and the chemical analysis correspond to the formula

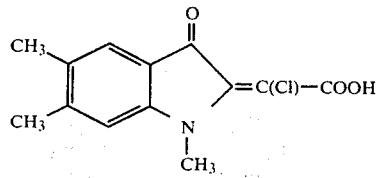

(2-carboxychloromethylene-1,5,6-trimethyl-indoxyl or chloro-(1,5,6-trimethyl-3-oxa-[2H]-indol-2-ylidene)-acetic acid).

If, in the above example, with an otherwise identical procedure, 21.8 g (0.1 mol) of the acid chloride of monomethyl 2,3-dichloromaleate are used in place of 16.7 g of dichloromaleic anhydride, 7.4 g of 2-carboxychloromethylene-1,5,6-trimethylindoxyl are obtained. In this case, the ester group in the starting material is saponified under the indicated reaction conditions.

EXAMPLE 2

125 g (0.9 mol) of powdered anhydrous AlCl$_3$ in 200 ml of 1,2-dichloroethane are initially introduced into a stirred flask provided with a HCl outlet and cooled to 0° C. with an external icebath. 44.7 g (0.3 mol) of N-ethyl-3,4-dimethylaniline are then added dropwise at 0°–3° C. in the course of 30 minutes and the resulting suspension is stirred for 30 minutes at this temperature. 48.3 g (0.28 mol) of dichloromaleic anhydride are then added in small portions at the same temperature and the suspension is stirred for 20 hours at 20°–25° C. and then for 1 hour at 40° C. The resulting blackish coloured solution is allowed to cool to 20°–25° C. and is then poured onto about 1,000 g of ice, the mixture is stirred for 30 minutes and the resulting black-blue emulsion is diluted with 500 ml of ethyl acetate. The two phases are separated in a separating funnel. The aqueous phase is further extracted with 250 ml of ethyl acetate and then discarded. The combined organic phases are washed with 300 ml of water, whereupon a blue-black precipitate forms. This is filtered off with suction and dried. This gives 24 g of blue-black crystals having a melting point of 130° C. (decomposition). The ethyl acetate phase is dried and filtered and the filtrate is concentrated to 100 ml, whereupon a blue-black precipitate forms. After filtering off and drying, this gives a further 13.6 g of blue-black crystals which, according to the thin layer chromatogram, are identical to the first crystalline product. The resulting crystalline product contains only slight impurities and can be used direct for further reactions. The product can be recrystallised from suitable solvents, such as glacial acetic acid. Such recrystallisation is, however, not necessary. Total yield=37.6 g (46.1% of theory).

NMR spectrum (60 Megahertz, δ values in ppm, DMSOd$_6$): 1.40 (t, J=7 Hz, 3H, CH$_3$); 2.26 (s, 3H, CH$_3$ on the aromatic nucleus); 2.31 (s, 3H, CH$_3$ on the aromatic nucleus); 4.20 (q, J=7 Hz, 2H, CH$_2$); 6.80 (s, 1H, aromatic); 7.50 (s, 1H, aromatic); (COOH cannot be discerned in DMSOd$_6$).

The spectroscopic data from NMR, MS and IR correspond to the formula

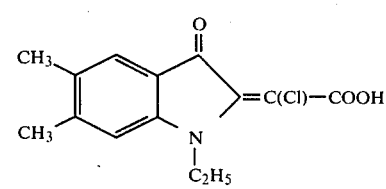

(2-carboxychloromethylene)-1-ethyl-5,6-dimethyl-indoxyl or chloro-(1-ethyl-5,6-dimethyl-3-oxa-[2H]-indol-2-ylidene)-acetic acid).

Using equivalent amounts of N-methyl-3-methylaniline, N-methyl-4-methylaniline and N-n-butyl-3,4-dimethylaniline, 2-carboxychloromethylene-1,5-dimethylindoxyl [chloro-(1,5-dimethyl-3-oxa[2H]indol-2-ylidene)-acetic acid] having a melting point of 235°–238° C., 2-carboxychloromethylene-1,6-dimethylindoxyl [chloro-(1,6-dimethyl-3-oxa[2H]-indol-2-ylidene)-acetic acid] having a melting point of 118°–122° C. and 1-n-butyl-2-carboxychloromethylene-5,6-dimethylindoxyl [chloro-(1-n-butyl-5,6-dimethyl-3-oxa[2H]indol-2-ylidene)-acetic acid] having a melting point of 172°–175° C. are prepared by the process described in the above examples.

If equivalent amounts of 2,3-dibromomaleic anhydride are reacted with N-methyl-3,4-dimethylaniline this gives 2-carboxy-bromomethylene-1,5,6-trimethyl-indoxyl [bromo-(1,5,6-trimethyl-3-oxa[2H]indol-2-ylidene)-acetic acid] having a melting point of 163°–165° C.

EXAMPLE 3

(a) 10.6 g of the 2-carboxychloromethylene-1,5,6-trimethylindoxyl prepared according to Example 1 are dissolved in 150 ml of ethanol. 6.8 g of piperidine in 30 ml of ethanol are then added dropwise at 50° C. and the solution is kept at 50° C. for one hour. It is diluted to 600 ml with ice-water, 45 ml of concentrated hydrochloric acid are added and the crude product is filtered off and purified in the manner described under c). After recrystallization from methanol, 3-hydroxy-1,5,6-trimethyl-indolyl-2-glyoxylic acid of the formula

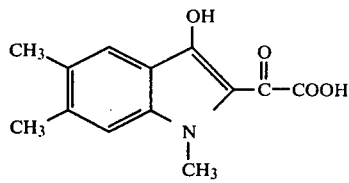

melts at 195°–197° C. The same product can also be obtained according to process variants (b) or (c) described below:

(b) 5.4 g of guanidine carbonate are added slowly to 7.8 g of 2-carboxychloromethylene-1,5,6-trimethyl-indoxyl in 50 ml of glacial acetic acid. The solution is then stirred for 24 hours at 60° C. and diluted with ice-water and the crude product which has separated out is purified in the manner described under (c).

(c) A mixture of 5.0 g of 2-carboxychloromethylene-1,5,6-trimethyl-indoxyl in 26 ml of dimethylsulphoxide and 4 ml of water is stirred at 70° C. for one hour, 100 ml of water are added and the mixture is stirred at 65° C. for 30 minutes. It is cooled and the crystals which have separated out are filtered off. The crystals are washed with 50 ml of cold water and dissolved in a mixture of 300 ml of water and 20 ml of 30% strength sodium hydroxide solution. The solution is filtered through a layer of Hyflo. The filtrate is rendered acid to Congo Red with concentrated hydrochloric acid and the crystals which have separated out are filtered off, washed with 100 ml of water and dissolved in 30 ml of 2 N sodium hydroxide solution. The aqueous alkaline solution is filtered through a layer of Hyflo. The filtrate is rendered acid with 2 N hydrochloric acid and the dark red crystals are filtered off; melting point 194°–196° C.

EXAMPLE 4

The 2-carboxychloromethylene-1,5,6-trimethyl-indoxyl prepared according to Example 1 is converted to 2-methoxycarbonylchloromethylene-1,5,6-trimethyl-indoxyl [methyl chloro-(3-oxa-1,5,6-trimethyl-[2H]-indol-2-ylidene)-acetate] of the formula

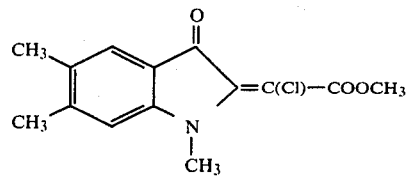

in a manner which is known per se, by reaction with dimethyl sulphate.

A solution of 32 g (0.114 mol) of 2-methoxycarbonyl-chloromethylene-1,5,6-trimethyl-indoxyl in 100 ml of ethanol is initially introduced and a solution of 19.2 g (0.228 mol) of piperidine in 50 ml of ethanol is added dropwise in the course of 30 minutes at 20°–25° C. The dark red solution is then stirred for 4 hours at 20°–25° C. 200 ml of 10% strength aqueous sulphuric acid are then added dropwise in the course of 30 minutes, with ice-cooling, and the mixture is stirred thoroughly for 1 hour at 20°–25° C. The dark brown suspension is filtered with suction and the material on the filter is washed with water and dried at 60° C. and 100 mm Hg. This gives 25.7 g of blackish crystals of methyl 3-hydroxy-1,5,6-trimethyl-indolyl-2-glyoxylate of the formula

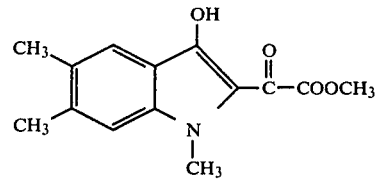

which still contain a small amount of impurities. Recrystallisation from ethyl acetate with the addition of active charcoal gives yellow-greenish crystals having a melting point of 169°–171° C.

EXAMPLES 5–7

In a manner analogous to that described in the preceding Examples 3 and 4, methyl 1-ethyl-5,6-dimethyl-3-hydroxyindolyl-2-glyoxylate having a melting point of 142°–143° C. (from cyclohexane) can be prepared starting from 1-ethyl-2-carboxychloromethylene-5,6-dimethyl-indoxyl, via 1-ethyl-5,6-dimethyl-2-methoxycarbonylchloromethylene-indoxyl having a melting point of 110°–111° C. (from ethyl acetate).

1,6-Dimethyl-3-hydroxy-indolyl-2-glyoxylic acid and 1-n-butyl-5,6-dimethyl-3-hydroxy-indolyl-2-glyoxylic acid and also the methyl esters thereof can also be obtained in an analogous manner.

EXAMPLE 8

23 ml of a 1 N aqueous solution of sodium hydroxide are added to a solution of 3.0 g of methyl 3-hydroxy-1,5,6-trimethyl-indolyl-2-glyoxylate in 200 ml of methanol and the mixture is stirred for 20 hours at room temperature (20°–25° C.). The suspension is then evaporated to dryness under reduced pressure at 40° C. The residue is dissolved in 300 ml of water. The aqueous solution is acidified with 30 ml of 2 N hydrochloric acid and the dark red suspension which has separated out is extracted with 700 ml of ethyl acetate. The organic phase is then shaken with 100 ml of 0.5 N sodium bicarbonate solution, whereupon the sodium salt of 3-hydroxy-1,5,6-trimethylindolyl-2-glyoxylic acid separates out as orange crystals. The product is filtered off and dried under 0.01 mm Hg at 60° C. It contains one mol of water of crystallisation and melts at 235° C. with decomposition. After recrystallisation from methanol, it melts at 234°–235° C.

Use Examples (A) Tablets containing 0.1 g of active compound, for example methyl 3-hydroxy-1,5,6-trimethyl-indolyl-2-glyoxylate, are prepared as follows:
Composition (for 1,000 tablets):

| | |
|---|---|
| active compound | 100.00 g |
| lactose | 50.00 g |
| wheat starch | 73.00 g |
| colloidal silica | 13.00 g |
| magnesium stearate | 2.00 g |
| talc | 12.00 g |
| water | q.s. |

The active compound is mixed with a portion of the wheat starch and with the lactose and the colloidal silica and the mixture is forced through a sieve. A further portion of the wheat starch is mixed to a paste with five times the amount of water on a waterbath and the above powder mixture is kneaded with this paste until a slightly plastic mass has formed. The plastic mass is pressed through a sieve of about 3 mm mesh width and dried and the dry granules are again forced through a sieve. The remaining wheat starch, the talc and the magnesium stearate are then mixed in and the resulting mixture is pressed to give tablets of 0.25 g.

(B) An approximately 2% strength aqueous solution, which is suitable for inhalation, of an active compound which is water-soluble in the free form or in the form of the sodium salt can be prepared, for example, in the following composition:
Composition

| | |
|---|---|
| active compound, for example sodium 3-hydroxy-1,5,6-trimethyl-indolyl-2-glyoxylate | 2,000 mg |
| stabiliser, for example the disodium salt of ethylenediaminetetraacetic acid | 10 mg |
| preservative, for example benzalkonium chloride water, freshly distilled | 10 mg to make up to 100 ml |

Preparation

The active compound is dissolved in freshly distilled water with the addition of the equimolar amount of 2 N sodium hydroxide solution. The stabiliser and the preservative are then added. After all of the components have dissolved completely, the resulting solution is made up to 100 ml and filled into small bottles and these are sealed gas-tight.

What is claimed is:
1. A compound of formula Ia

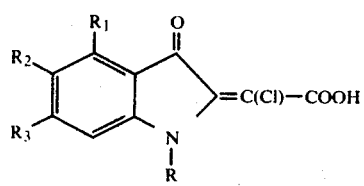

in which
R is lower alkyl having 1 to 4 carbon atoms; 2-hydroxy-lower alkyl, 3-hydroxy-lower alkyl or 2,3-dihydroxy-lower alkyl, said lower alkyl groups having 2 to 4 carbon atoms; or 2-lower alkoxy-lower alkyl or 3-lower alkoxy-lower alkyl, said alkoxy-alkyl groups having a total of 3 or 4 carbon atoms, and wherein $R_1$ is hydrogen, $R_2$ is methyl and $R_3$ is chloro, or $R_2$ is bromo and $R_3$ is methyl; or $R_2$ and $R_3$ are methyl; or wherein $R_1$ is methyl, $R_2$ is hydrogen, and $R_3$ is methyl; or wherein $R_1$ and $R_2$ are hydrogen and $R_3$ is methyl or ethyl; or wherein $R_1$ and $R_3$ are hydrogen, and $R_2$ is methyl, ethyl, isopropyl or n-butyl; or wherein $R_1$ is hydrogen, and $R_2$ and $R_3$ together are alkylene having 3 carbon atoms.

2. A compound according to claim 1 of the formula

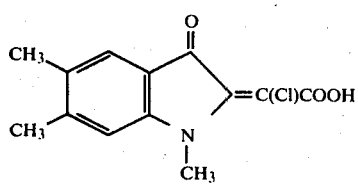

3. A compound according to claim 1 of the formula

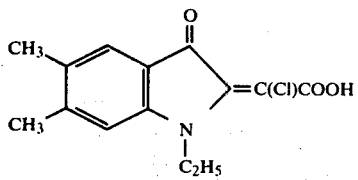

4. A compound according to claim 1 of the formula

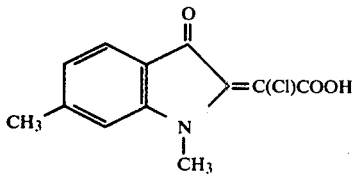

5. A compound according to claim 1 wherein R is alkyl having 1 to 4 carbon atoms, $R_1$ is hydrogen and $R_2$ and $R_3$ are methyl; or R and $R_2$ are methyl, and $R_1$ and $R_3$ are hydrogen; or R and $R_3$ are methyl, and $R_1$ and $R_2$ are hydrogen.

6. The compound 2-carboxybromomethylene-1,5,6-trimethylindoxyl,

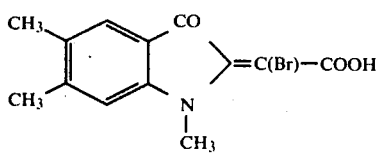

7. A process for the preparation of a compound of formula Ib

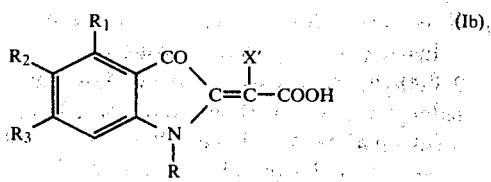

wherein
R is lower alkyl having 1 to 4 carbon atoms; 2-hydroxy-lower alkyl, 3-hydroxy-lower alkyl or 2,3-dihydroxy-lower alkyl, said lower alkyl having 2 to 4 carbon atoms; or 2-lower alkoxy-lower alkyl or 3-lower alkyl-lower alkyl, said alkoxy-alkyl groups having a total of 3 or 4 carbon atoms; and wherein $R_1$ is hydrogen, $R_2$ is methyl and $R_3$ is chloro, or $R_2$ is bromo and $R_3$ is methyl; or $R_2$ and $R_3$ are methyl; or wherein $R_1$ is methyl, $R_2$ is hydrogen, and $R_3$ is methyl; or wherein $R_1$ and $R_2$ are hydrogen, and $R_3$ is methyl or ethyl; or wherein $R_1$ and $R_3$ are hydrogen, and $R_2$ is methyl, ethyl, isopropyl or n-butyl; or wherein $R_1$ is hydrogen, and $R_2$ and $R_3$ together are alkylene having 3 carbon atoms; and X' is chlorine or bromine, which consists essentially of reacting a compound of formula IIb

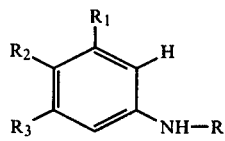

wherein $R_1$, $R_2$ and $R_3$ are defined as above and R is alkanoyl having 1–6 carbon atoms or benzoyl, in substantially stoichiometric amounts with a compound of formula III

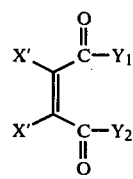

wherein the two X's independently of one another are chlorine or bromine, and one of $Y_1$ and $Y_2$ is halogen and the other is —OH or —O—alkyl having 1–6 carbon atoms; or $Y_1$ and $Y_2$ together form the grouping —O—; in the melt or in an inert organic solvent selected from the group consisting of chlorinated aliphatic hydrocarbons, chlorinated atomatic hydrocarbons, n-pentane, n-hexane, nitrobenzene, nitromethane and carbon disulfide, at a temperature between about 0° C. and 130° C. in the presence of an excess molar amount of a Lewis acid selected from the group consisting of aluminum chloride, aluminum bromide, zinc chloride, tin tetrachloride, boron trifluoride, ferric chloride, phosphorus trichloride, phosphorus oxychloride, antimony pentafluoride, antimony pentachloride and titanium tetrachloride to give a compound of formula IVb

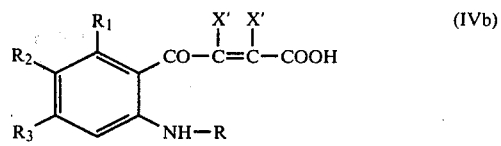

wherein
$R_1$, $R_2$, $R_3$, R and X' are as defined above; in the reaction mixture; and then
adding the reaction mixture containing the compound of formula IVb to an aqueous medium at a temperature between about 0° C. and 100° C. to give the compound of formula Ib.

8. A process according to claim 7 where R is alkyl having 1 to 4 carbon atoms, $R_1$ is hydrogen and $R_2$ and $R_3$ are methyl; or R and $R_2$ are methyl, and $R_1$ and $R_3$ are hydrogen; or R and $R_3$ are methyl, and $R_1$ and $R_2$ are hydrogen.

9. A process according to claim 7 where the compound of formula III is dichloromaleic anhydride, dibromomaleic anhydride or the acid chloride of monomethyl 2,3-dichloromaleate.

10. A process according to claim 7 wherein R is alkyl having 1 to 4 carbon atoms, $R_1$ is hydrogen and $R_2$ and $R_3$ are methyl; and the compound of formula III is dichloromaleic anhydride, dibromomaleic anhydride, or the acid chloride of monomethyl 2,3-dichloromaleate.

11. A process according to claim 7 wherein R and $R_2$ are methyl; and $R_1$ and $R_3$ are hydrogen; or R and $R_3$ are methyl, and $R_1$ and $R_2$ are hydrogen; and the compound of formula III is dichloromaleic anhydride.

12. A process according to claim 7 wherein the aqueous medium to which the reaction mixture containing the compound of formula IVb is added consists essentially of water and an inert organic solvent selected from the group consisting of aliphatic hydrocarbons, aromatic hydrocarbons, chlorinated aliphatic hydrocarbons, chlorinated aromatic hydrocarbons, aliphatic ethers, cyclic ethers, ethylene glycol monoalkyl ethers and ethylene glycol dialkyl ethers.

13. A process according to claim 7 wherein the aqueous medium to which the reaction mixture containing the compound of formula IVb is added consists essentially of water and an organic or inorganic base.

14. A process according to claim 7, wherein dichloromaleic anhydride is used as the compound of the formula III.

* * * * *

UNITED STATES PATENT AND TRADEMARK OFFICE
CERTIFICATE OF CORRECTION

PATENT NO. : 4,260,545
DATED : APRIL 7, 1981
INVENTOR(S) : NIKLAUS BUHLER ET AL.

It is certified that error appears in the above—identified patent and that said Letters Patent is hereby corrected as shown below:

Claim 7, Column 11, Line 15 reads:

"or 3-lower alkyl-lower alkyl, said alkoxy-alkyl"

should reads:

"or 3-lower alkoxy-lower alkyl, said alkoxy-alkyl"

Signed and Sealed this

Seventh Day of July 1981

[SEAL]

Attest:

RENE D. TEGTMEYER

Attesting Officer     Acting Commissioner of Patents and Trademarks